United States Patent
Pu et al.

(10) Patent No.: US 11,693,012 B1
(45) Date of Patent: Jul. 4, 2023

(54) SCREENING METHOD

(71) Applicant: SUZHOU INSTITUTE OF NANO-TECH AND NANO-BIONICS (SINANO), CHINESE ACADEMY OF SCIENCES, Suzhou (CN)

(72) Inventors: Kefeng Pu, Suzhou (CN); Jiong Li, Suzhou (CN); Min Jiang, Suzhou (CN)

(73) Assignee: SUZHOU INSTITUTE OF NANO-TECH AND NANO-BIONICS (SINANO), CHINESE ACADEMY OF SCIENCES, Suzhou (CN)

( * ) Notice: Subject to any disclaimer, the term of this patent is extended or adjusted under 35 U.S.C. 154(b) by 0 days.

(21) Appl. No.: 18/010,466

(22) PCT Filed: Feb. 26, 2021

(86) PCT No.: PCT/CN2021/078117
§ 371 (c)(1),
(2) Date: Dec. 15, 2022

(87) PCT Pub. No.: WO2022/095311
PCT Pub. Date: May 12, 2022

(30) Foreign Application Priority Data

Nov. 3, 2020 (CN) .......................... 202011211640.9

(51) Int. Cl.
*G01N 33/68* (2006.01)
*G01N 15/14* (2006.01)
(Continued)

(52) U.S. Cl.
CPC ..... *G01N 33/6854* (2013.01); *G01N 15/1434* (2013.01); *G01N 33/56966* (2013.01); *G01N 33/582* (2013.01); *G01N 2015/149* (2013.01)

(58) Field of Classification Search
CPC .......... G01N 33/6854; G01N 15/1434; G01N 33/56966; G01N 33/582; G01N 2015/149
See application file for complete search history.

(56) References Cited

U.S. PATENT DOCUMENTS 5,504,337 A * 4/1996 Lakowicz .......... G01N 21/6408
356/318
10,329,594 B1 6/2019 Forman
(Continued)

FOREIGN PATENT DOCUMENTS

CN 101303356 A 11/2008
CN 104818295 A 8/2015
(Continued)

OTHER PUBLICATIONS

Edmund Newman, et al., Rapid selection of mammalian cells secreting large amounts of therapeutic proteins or peptides, Nature Methods, 2007, pp. i-ii.

*Primary Examiner* — Kiho Kim
(74) *Attorney, Agent, or Firm* — Bayramoglu Law Offices LLC

(57) ABSTRACT

A screening method is provided. Cells secreting target antibodies are screened by mixing candidate cells labeled with a first fluorescent molecule, a capture antigen and a labeled antibody against a target antibody and incubating, labeling using a high content cell imager and sorting using flow cytometry so as to screen cells secreting target antibodies. The screening method disclosed in the present application can automatically complete the labeling and sorting of target candidate cells in high throughput by labeling with a fluorescent molecule in combination with high-content cell imager and flow cytometer, so as to provide sufficient quantity of cells for subsequent amplification to obtain their antibody sequences and screen affinity anti-
(Continued)

bodies. This method greatly improves the screening efficiency.

20 Claims, 2 Drawing Sheets

Specification includes a Sequence Listing.

(51) Int. Cl.
*G01N 33/58* (2006.01)
*G01N 33/569* (2006.01)

(56) References Cited

U.S. PATENT DOCUMENTS

| 10,895,575 B2* | 1/2021 | Manaresi | G01N 33/57423 |
| 2017/0102314 A1* | 4/2017 | Diebold | G01N 15/1425 |
| 2020/0124532 A1* | 4/2020 | Lebeck | G01N 21/6428 |

FOREIGN PATENT DOCUMENTS

| CN | 110887961 A | 3/2020 |
| CN | 110887967 A | 3/2020 |

\* cited by examiner

SCREENING METHOD

CROSS REFERENCE TO THE RELATED APPLICATIONS

This application is the national phase entry of International Application No. PCT/CN2021/078117, filed on Feb. 26, 2021, which is based upon and claims priority to Chinese Patent Application No. 202011211640.9, filed on Nov. 3, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBNJLF041-PKG_Sequence_Listing.txt, created on 10/10/2022, and is 7,864 bytes in size.

TECHNICAL FIELD

The present application relates to the field of biological technologies, particularly to a screening method.

BACKGROUND

Since the establishment of a hybridoma technology by Kohler and Milstein in 1975, thousands of different monoclonal antibodies have been produced. Some of them have been used for scientific research and detection, some of them have been used for clinical diagnosis, and some of them have been used for treating various diseases, such as tumors, immune system diseases, and cardiovascular and cerebrovascular diseases. Monoclonal antibodies have high commercial value. Among the top 10 best-selling drugs in 2019, therapeutic monoclonal antibodies contributed 73% of the total sales, reaching $87 billion. It is estimated that by 2025, the global therapeutic monoclonal antibody market will reach 300 billion US dollars. For a drug target, many antibodies need to be screened before it is possible to select a candidate antibody drug that can be used in clinical research, so an efficient and reliable antibody discovery platform is essential.

So far, the main monoclonal antibody discovery technologies are divided into a hybridoma technology, a surface display technology and a single B cell technology.

The hybridoma technology is developed from a cell fusion technology. Spleen B lymphocytes and myeloma cells are fused to form a B lymphocyte myeloma cell hybrid. Only this hybrid can be proliferated and survive indefinitely and rapidly in a Hat culture medium and secrete antibodies. Although this technology can screen specific antibodies, this method has the obvious disadvantages:

(1) this method needs to be manually operated, and there are too many operations and repeated steps;

(2) this method is slow in speed and low in efficiency, and cannot meet requirements for high-flux screening;

(3) this method cannot ensure mono-cloning, and sub-cloning is required for 3-4 times, which wastes labors and is time-consuming;

(4) limited dilution is conducted before ELISA detection, and which clone meets the requirements of antigen specificity is not known.

Therefore, all clones need to be identified by ELISA for at least once. After 45 years of development, some manually operated equipment that can reduce hybridoma screening has been produced, such as ClonePix system. The system uses a semi-solid culture method to grow cells on the culture medium to form single independent and dispersed monoclonal antibodies on the culture medium. A fluorescent labeled clone detection reagent is added to the semi-solid culture medium. With the extension of clone growth time, more fluorescent protein complexes can gather around the clones, and then the clones to be selected are picked one by one by a leader. Although this technology reduces the manual operation of hybridoma screening, it also has some disadvantages. For example, first of all, it is needed to develop a proper culture medium so as to grow hybridoma on the semi-solid culture medium. Secondly, the precision of automatically picking comes is greatly affected by the size and density of clones. Too small clone can affect identification and picking. Too dense clone can easily affect the monoclonal nature of the picked clone. Finally, a robot arm requires high picking precision, so equipment needs to careful daily maintenance.

Another major antibody discovery method is the surface display technology. A phage display and yeast display technology is widely used. This principle is to amplify a heavy chain variable region (VH) and light chain variable region (VL) of an antibody of B lymphocyte via PCR, insert the amplified fragment into a vector, and perform fusion expression on the Fab fragment or single chain antibody (scFv) of the antibody molecule and a single-stranded phage coat protein or yeast surface protein, so as to display the antibody on the surface of the phage or yeast. Monoclonal antibodies specific to target antigens can be obtained after affinity adsorption-elution-amplification and other steps by using an antigen screening method. However, in this method, the heavy antibody chain and the light antibody chain of the variable region are randomly combined, which makes a large part of pairing meaningless. Furthermore, most of the antibodies screened from these display libraries need to be further matured to meet the affinity requirements.

The single B cell technology has been developed in recent years. This technology can directly isolate and express antibodies from single B lymphocytes of mammals or humans, which can save plenty of screening time. At present, the main single B cell technology is aimed at memory B cells, because corresponding IgG is expressed on the surface of the cell, which can be sorted (flow sorting, magnetic sorting, or microfluidic sorting) after coupling with labeled antigens (fluorescence or magnetism), thereby achieving high-throughput screening. Lotta von BOEHMER et al. use flow sorting to sort memory B cells that can bind to antigens into a 96 well PCR plate for amplification of variable regions of heavy and light chains, and then express and screen specific antibodies. However, such the method can only be used for memory B cells that express IgG on the surface of the cell, and the antibodies expressed by plasma cells cannot be detected by the method because they are secreted. Alison M Clargo et al. established a fluorescent foci method in which cells secreting specific antibodies were taken through microscopic operation, then amplification of variable regions of heavy chain and light chain and expression of the antibody were conducted. But, this method needs to microscopic operation to take out target cells, which is time-consuming and wastes labor, and cannot be conducted in high throughput.

In view of this, the present application is hereby proposed.

SUMMARY

The objective of the present application is to provide a screening method, more particularly to an antibody and a screening method of a cell secreting the antibody.

The present application is realized as follows:

In one aspect, the present application provides a method for screening cells secreting target antibodies, comprising the following steps:

Step (a): labeling a candidate cell with a first fluorescent molecule;

Step (b): adding the candidate cell labeled with the first fluorescent molecule and a labeled antibody against the target antibody into a container fixed with a capture antigen to be mixed and incubated to obtain cellular fluid; wherein, the capture antigen can specifically bind to the target antibody; the labeled antibody is labeled with a second fluorescent molecule;

the first fluorescent molecule has the following properties: the fluorescent light emitted after the first fluorescent molecule is excited by first exciting light is different from that emitted after the second fluorescent molecule is excited by the first exciting light; the first fluorescent molecule is in a photo-activated state or a photo-converted state, which emits first fluorescent light after being excited by third exciting light under the photo-activated state or the photo-converted state; furthermore, the first fluorescent light emits second fluorescent light after being directly excited by third exciting light instead of second exciting light; the wavelength of the first fluorescent light is different from that of the second fluorescent light, or the wavelength of the first fluorescent light is the same as that of the second fluorescent light but fluorescence intensities are different; wherein, the wavelength of the first exciting light is different from that of the second exciting light; the wavelength of the second exciting light is different from that of the third exciting light;

the wavelength of the fluorescent light emitted after the second fluorescent molecule is excited by first exciting light is different from that of the second exciting light;

Step (c): observing the cellular fluid using a high content cell imager, exciting the second fluorescent molecule by using the first exciting light to emit fluorescent light and screening the candidate cell surrounded by the fluorescent light, and labeling the candidate cell as a target candidate cell; then irradiating the target candidate cell with the second exciting light so that the first fluorescent molecule labeling the target candidate cell is in the photo-activated state or the photo-converted state;

Step (d): sorting the candidate cell in the cellular fluid using flow cytometry wherein in the process of sorting, the candidate cell processed in Step (c) is irradiated using the third exciting light and the target candidate cell emitting the first fluorescent light is sorted, namely, the cell secreting the target antibody.

The screening method provided by the present application can screen a cell secreting the antibody in high throughput. The screening principle of the method is as follows:

Since the target antibody is secreted, and the target antibody is secreted to the outside of the cell and distributed around the candidate cell, when the candidate cell is irradiated with the first exciting light, the second fluorescent molecule can be excited to emit fluorescent light. at this moment, the candidate cell that can secrete the target antibody can be surrounded by fluorescent light, while the candidate cell that cannot secrete the target antibody is surrounded by fluorescent light; in view of this phenomenon, the candidate cell that can secrete the antibody can be preliminarily determined; then the above candidate cell is selectively excited by the second exciting light so that the labeled first fluorescent molecule is in a photo-activated state or a photo-converted state; and then in the screening step using a flow cytometer, when excited by the third exciting light, the first fluorescent molecule in the photo-activated state or the photo-converted state emits the first fluorescent light, and the fluorescent molecule that is not excited by the second exciting light emits the second fluorescent light; accordingly, the candidate cell that can secrete the target antibody is distinguished and from the candidate cell that cannot secrete the target antibody and screened according to the difference between the first fluorescent light and the second fluorescent light.

It can be seen from the screening principle that for the cell screening of the secreting type antibody, the screening method provided in the present application can automatically complete the labeling and sorting of the target candidate cell in high throughput by labeling with the fluorescent molecule in combination with a high-content cell imager and a flow cytometer, so as to provide a sufficient quantity of cell bases for subsequent amplification of antibody sequences and screening of affinity antibodies, thereby improving the screening efficiency.

It should be noted that the "fluorescence difference" in "the fluorescent light emitted by the first fluorescent molecule after being excited by the first exciting light is different from the fluorescent light emitted by the second fluorescent molecule after being excited by the first exciting light" as described above means that the wavelengths of the fluorescent lights of the two fluorescent molecules are different, or the second fluorescent molecule emits the fluorescent light but the first fluorescent molecule does not emit the fluorescent light. The type of the second fluorescent molecule can be reasonably selected according to the type of the first fluorescent molecule, as long as the fluorescent light of the second fluorescent molecule can be distinguished from the fluorescent light of the first fluorescent molecule under the excitation of the first exciting light. According to the above contents, those skilled in the art can easily understand that the wavelengths of the first exciting light and the second exciting light are different to avoid mutual influence.

In an alternative embodiment, the first fluorescent molecule is selected from a photo-activated fluorescent protein and a photo-activated fluorescent protein.

In an alternative embodiment, in Step (d), when the cellular fluid is used to flow through the flow cytometry for sorting, the second fluorescent molecule is a fluorescent molecule which does not emit fluorescent light under the excitation of the third exciting light, or a fluorescent molecule in which the wavelength of the fluorescent light emitted under the excitation of the third exciting light is different from that of the first fluorescent light.

When the cellular fluid is directly sorted, it contains a labeled antibody, and the fluorescence property of the second fluorescent molecule should satisfy the following conditions (a): the second fluorescent molecule does not emit the fluorescent light under the excitation of the third exciting light, or the wavelength of the fluorescent light emitted under the excitation of the third exciting light is different from the wavelength of the first fluorescent light. Under the premise of meeting this condition, the fluorescence interference generated by the second fluorescent molecule in the sorting can be avoided. When the solution used for sorting contains or does not contain the labeled antibody, the second fluorescent molecule cannot satisfy the above condition (a).

Whether to select the cellular fluid for direct sorting can be determined according to the immobilization method of the captured antigen.

For example, when the captured antigen is immobilized in a container (e.g., cell culture dish) by cells (e.g., adherent cells) expressing the antigen, in this case, the candidate cell is difficult to isolate, so the cellular fluid can be digested to form a cell suspension and then directly used for subsequent sorting. In this case, the cellular fluid used for sorting contains the labeled antibody. In this case, the second fluorescent molecule needs to satisfy the above condition (a).

For another example, when the captured antigen is directly immobilized or coated in the container (such as the cell culture dish) by other media (such as microspheres or magnetic beads), in this case, the candidate cell can be easily isolated from the cellular fluid by washing. In this case, the candidate cell can be separately isolated, and then diluted with a suitable diluent for subsequent analysis steps. In this case, the cellular fluid used for sorting does not contain the labeled antibody, and the second fluorescent molecule cannot meet the above condition (a).

In an alternative embodiment, the container contains the adherent cell over-expressing the captured antigen. The captured antigen is immobilized in the container by the adherent cell expressing the antigen. The antibody secreted by the candidate cell can be concentrated around the candidate cell by the immobilized capture antigen, which is convenient for fluorescence observation.

In an alternative embodiment, after the treatment in Step (c), the cellular fluid is digested to obtain a cell suspension, and the cell suspension is sorted by flow cytometry.

In an alternative embodiment, the photo-activated fluorescent protein is PA-GFP.

In an alternative embodiment, when the first fluorescent molecule is a PA-GFP protein, the wavelength range of the first exciting light is not within a range of 390 nm-415 nm, the wavelength range of the second exciting light is 390 nm-450 nm, and the wavelength range of the third exciting light is 450 nm-550 nm (the maximum wavelength of the exciting light is 504 nm).

When the first fluorescent molecule is the PA-GFP protein, the candidate cell surrounded by the second fluorescent molecule is screened by using a high content cell imager and then irradiated using intense violet light, that is, second exciting light (390 nm-450 nm), and therefore green fluorescent light produced by this variant is improved by 100 times. Through flow cytometry, the wavelength range of the emitting light of the candidate cell is 480 nm-600 nm (the maximum wavelength of the emitting light is 517 nm) after irradiation with the third exciting light with the exciting light wavelength range of 450 nm-550 nm (the maximum wavelength of the exciting light is 504 nm). At this moment, when the non-candidate cell that is not irradiated by the second exciting light is irradiated by the third exciting light, it emits weak green fluorescent light, and the wavelength range of the emitting light is 480 nm-600 nm (the maximum wavelength of the emitting light is 515 nm). By utilizing the fluorescence intensities of different emitted lights, the photo-activated candidate cell with the PA-GFP protein and capable of secreting the target antibody can be sorted.

In an alternative embodiment, the photo-converted fluorescent protein is selected from PS-CFP2, PS-CFP, mEosFP, tdEosFP, dEosFP, WtEosFP, Kaede, Dendra2 and KikGR.

In an alternative embodiment, when the first fluorescent molecule is PS-CFP2 protein, the wavelength range of the first exciting light is not within a range of 390 nm-450 nm, the wavelength range of the second exciting light is 390 nm-415 nm, and the wavelength range of the third exciting light is 420 nm-520 nm (the maximum wavelength of the exciting light is 490 nm);

When the first fluorescent molecule is PS-CFP2 protein, the candidate cell surrounded by the fluorescent light of the second fluorescent molecule is screened using the high-content cell imager and then irradiated with intense violet light, that is, second exciting light (390 nm-415 nm), and therefore the candidate cell with blue-green fluorescent light is photo-converted so that the blue-green fluorescent light becomes green fluorescent light. By flow cytometry, under the excitation of the third exciting light, the wavelength range is 420 nm-520 nm (the maximum wavelength of the exciting light is 490 nm), and the wavelength range of the emitting light of the candidate cell irradiated by the second exciting light is 450 nm-600 nm (the maximum wavelength of the emitting light is 511 nm). At this moment, the candidate cell that is not irradiated by the second exciting light do not emit the fluorescent light when being irradiated by the third exciting light. Therefore, the candidate cell secreting the target antibody can be sorted.

In an alternative embodiment, when the first fluorescent molecule is Kaede protein, the wavelength range of the first exciting light is not within a range of 350 nm-400 nm, the wavelength range of the second exciting light is 350 nm-400 nm, and the wavelength range of the third exciting light is 500 nm-600 nm (the maximum wavelength of the exciting light is 572 nm).

When the first fluorescent molecule is Kaede protein, the candidate cell surrounded by the fluorescent light of the second fluorescent molecule is screened by using a high-content cell imager and then irradiated with intense violet light, that is, second exciting light (350 nm-400 nm). The candidate cell with green fluorescent light is photo-converted so that the green fluorescent light becomes red fluorescent light. By flow cytometry, under the excitation of the third exciting light, the wavelength range is 500 nm-600 nm (the maximum wavelength of the exciting light is 572 nm), and the wavelength range of the emitting light of the candidate cell irradiated by the second exciting light is 550 nm-650 nm (the maximum wavelength of the emitting light is 580 nm). At this moment, the candidate cell that is not irradiated by the second exciting light does not emit the fluorescent light when being irradiated by the third exciting light. Therefore, the candidate cell secreting the target antibody can be sorted.

In an alternative embodiment, when the first fluorescent molecule is KikGR protein, the wavelength range of the first exciting light is not within a range of 390 nm-415 nm, the wavelength range of the second exciting light is 390 nm-415 nm, and the wavelength range of the third exciting light is 500 nm-600 nm (the maximum wavelength of the exciting light is 583 nm).

When the first fluorescent molecule is KikGR protein, the candidate cell surrounded by the fluorescent light of the second fluorescent molecule is screened by using a high-content cell imager and then irradiated with strong violet light, that is, second exciting light (390 nm-415 nm), and the candidate cell with green fluorescent light is photo-converted so that the green fluorescent light becomes red fluorescent light. By flow cytometry, under the excitation of the third exciting light, the wavelength range is 500 nm-600 nm (the maximum wavelength of the exciting light is 583 nm), and the wavelength range of the emitting light of the candidate cell irradiated by the second exciting light is 550 nm-650 nm (the maximum wavelength of the emitting light is 593 nm). At this moment, the candidate cell that is not irradiated with the second exciting light does not emit the fluorescent light when being irradiated with the third exciting light. Therefore, the candidate cell secreting the target antibody can be sorted.

In an alternative embodiment, the candidate cell in Step (a) is selected from B lymphocytes, T cells, NK cells, HEK cells, CHO cells, bacteria and yeast.

The type of the candidate cell can be selected as needed, and any cells that are expected to secrete the target antibodies can be selected as the candidate cells of the present application. For example, a typical secreting type cell secreting the antibody includes B lymphocyte. In some embodiments, the candidate cell can also be derived from spleen cells, bone marrow cells, lymph node cells and the like from an immunized host animal.

However, it should be noted that it can be understood according to the screening principle that the method of the present application can be used for screening not only cells secreting antibodies, but also cells secreting any proteins. Therefore, applying the method of the present application to screen other cells secreting proteins also falls within the protective scope of the present application.

In an alternative embodiment, in Step (a), a method for labeling the candidate cells with the first fluorescent molecule is selected from methods shown in any one of (I)-(IV):

(I): introducing a nucleotide encoding the first fluorescent molecule into the candidate cell and allowing the nucleotide to express the first fluorescent molecule in the candidate cell;

(II): introducing the first fluorescent molecule into the candidate cell through electrotransfection;

(III): performing fusion expression on the first fluorescent molecule and an antibody of a cytomembrane surface specific marker of a candidate cell, so that the first fluorescent molecule is linked to the surface of the candidate cell through the specific binding of the antibody to the specific market; and (IV): labeling the first fluorescent molecule with a lipid, mixing the first fluorescent molecule labeled with the lipid with the candidate cell so that the first fluorescent molecule is linked to the surface of the candidate cell.

It should be noted that the method for labeling the first fluorescent molecule on the candidate cell is not limited to the above methods shown in (I)-(IV), and those skilled in the art can easily realize the labeling of the first fluorescent molecule according to the conventional technology in the art. Labeling the first fluorescent molecule on the candidate cell in other ways belongs to the protective scope of the present application. In addition, the first fluorescent molecule can be labeled on the surface or inside of the candidate cell, or on the surface and inside the cell.

In an alternative embodiment, the lipid is selected from DSPE-NHS, DSPE-PEG2000-NHS, DSPE-PEG3400-NHS, oleyl-PEG2000-NHS, oleyl-PEG4000-NHS and dioleoylphosphatidylethanolamine (DOPE)-PEG2000-NHS.

In an alternative embodiment, in Step (c), imaging is performed under a low power microscope to screen the target candidate cell; and then the target candidate cell is irradiated by the second exciting light by switching to a high-power microscope.

In an alternative embodiment, in order to avoid the suspension of the candidate cell and the dispersion of the secreted antibody, cells expressing the captured antigens can also be inoculated and expressed in a culture container containing an incubation system, or beads (e.g., magnetic beads) of the captured antigen may be connected therein. The surfaces of these cells or beads can also express or couple some capture molecules, such as anti-CD19 antibody, anti-B lymphocyte antibody, anti-CD19 scFv and other capture molecules, which can capture candidate cells without leaving them in a suspension state. Or, gelatin can be added into the incubation system to reduce the fluidity of cells and antibodies, which is conducive to detection and observation.

In an alternative embodiment, before performing Step (d), the cellular fluid obtained in Step (c) is digested into a single-cell suspension, and the single-cell suspension is sorted.

In an alternative embodiment, in Step (d), sorting can also be realized by using a micro-controlled flow chip.

In another aspect, the present application provides a method for screening a target antibody, comprising the following steps:

obtaining a cell secreting the target antibody using any method as described above; and acquiring a nucleotide sequence encoding the target antibody from the cell secreting the target antibody.

BRIEF DESCRIPTION OF THE DRAWINGS

In order to more clearly explain the technical solution of the embodiments of the present application, accompanying drawings used in the embodiments will be simply described below. It should be understood that the following drawings only show some embodiments of the present application, but should not be regarded as limiting the scope. For persons of ordinary skill in the art, other relevant drawings can also be obtained according to these drawings without creative efforts.

DETAILED DESCRIPTION OF THE EMBODIMENTS

Figure 1:
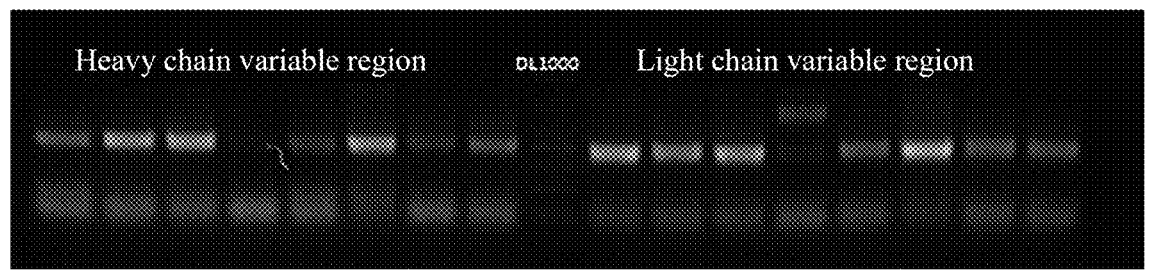
FIG. 1 is a schematic diagram of a heavy chain variable region sequence and a light chain variable region sequence of an antibody obtained by PCR, both of which are about 400 bp in size.

In order to make the objectives, technical solutions and advantages of the embodiments of the present application more clear, the technical solutions in the embodiments of the present application will be described clearly and completely below. If no specific conditions are indicated in the embodiments, the embodiments will be conducted according to conventional conditions or conditions recommended by a manufacturer. If the used reagents or instruments have no manufacturers, they are all conventional products that can be purchased in the market.

The features and performances of the present application are further described in detail below in combination with embodiments.

Example 1

This example takes an anti-PDL1 antibody and B lymphocytes as examples to explain a method for screening B lymphocytes secreting the anti-PDL1 antibody provided in this example. The method includes:

1. PDL1 Proteins were Used as Antigen Immune Mice. Refer to Conventional Methods in the Art.

2. Enrichment of B Lymphocytes

1) Spleen was taken from mice, placed in a 40 μm filter membrane and crushed, and single splenocytes were obtained through a filter screen and then placed in 50 ml of pre-cooled serum-free 1640 culture medium.

2) The splenocytes were centrifuged for 5 min under the conditions of 4° C. and 500 g.

3) The supernatant was discarded, and the cells were re-suspend to 10 ml 1×red split solution (BD bioscience, cat: 555899) and subjected to standing for 5 min at room temperature under dark conditions.

4) The re-suspended cells were added into 40 ml of serum-free 1640 culture medium and then centrifuged for 5 min under the conditions of 4° C. and 500 g.

5) The supernatant was discarded, and cell precipitates were re-suspended in 10 ml MACS Buffer (MACS Buffer: Miltenyi biotec order no. 130-091-221), evenly blown, stained with trypan blue, and finally counted.

6) $5 \times 10^7$ cells were taken and centrifuged for 5 min under the conditions of 4° C. and 500 g, and the supernatant was discarded.

7) 175 μl of MACS buffer, 25 μl of FcR Blocking Reagent and 50 μl of biotin antibody cocktail (Pan B Cell Isolation Kit II, mouse (Order No: 130-104-443)) were added, evenly mixed, and incubated for 5 min at 4° C.

8) The cell suspension was added into 150 μl of MACS buffer, 100 μl of Anti-Biotin Microbeads and then evenly mixed, and incubated for 10 min at 4° C.

9) An Ls column was equilibrated with 3 ml of buffer.

10) The cell suspension passed through the column (500 μl) to collect filtrate.

11) 3 ml of buffer was added again into the LS column, and the filtrate was collected to a centrifuge tube.

12) 3.5 ml of the resulting filtrate was candidate B lymphocyte.

3. Packaging Lentivirus Before Enrichment of B Lymphocytes 1) 293T cells densely grown were taken, with a dense of about 80%-90%, and a fresh culture medium (DMEM+10% FBS) was changed, namely, 10 ml/10 cm cell culture dish.

2) Two 2 ml centrifuge tubes were taken, 625 μl of DMEM culture medium and 18.75 μl of Lipofectamine3000 were added into tube 1. 625 μl of DMEM culture medium, 7.5 mg of psPAX2, 2.5 μg of PMD2G plasmid, 10 μg of PLVX-Kaede-IRES-PURO plasmid and 25 μl of P3000 were added into tube 2.

3) The solution in tube 1 was transferred into tube 2, and then the solution in the tube was evenly mixed with an oscillator and stood for 5 min.

4) 293T cells were taken out, the mixture was gently transferred into the cells to put back into an incubator.

5) After 48 h, the lentivirus supernatant was collected for the first time, and then the cells were added again into a 10 ml/10 cm fresh culture medium.

6) After 72 h, the lentivirus was collected for the second time, the virus supernatant was centrifuged for 2 h under the conditions of 4° C. and 60000 g, and the supernatant was discarded. The precipitate was re-suspended with an appropriate amount of PBS to obtain concentrated viruses with a titer of $10^7$ μ/ml.

4. B Lymphocytes were Infected by Viruses to Obtain B Lymphocytes Expressing Kaede Protein (First Fluorescent Molecule)

1) The isolated B lymphocytes were infected according to MOI=50 (10-100, preferably 50), transfected for 6 h (30 min-48 h, preferably 6 h), then 500 g of cell suspension was centrifuged for 5 min, and the supernatant was discarded to obtain B lymphocytes expressing Kaede protein.

5. Spread of Transfected B Lymphocytes

1) CHO-K1 cells over-expressing PDL1 (capture antigen) were inoculated into a cell culture dish one day before transfection.

2) The transfected B lymphocytes were spread into the dish, and the number of spread cells was preferably $2 \times 10^6$ ($2 \times 10^4$-$2 \times 10^7$). After culturing for 6-48 h, the medium was gently aspirated and discarded, and a Goat pAb to Ms IgG (Aleax Flour 647, abcam, cat: ab150115) staining solution (containing a second fluorescent molecule Aleax Flour 647 labeled secondary antibody) prepared with a fresh culture medium was added to avoid that B cells were disturbed, wherein the working concentration was 0.2 μg/ml. After incubation for 30 min with 5% $CO_2$ at 37° C., the staining solution was gently sucked and discarded, and a fresh culture medium was changed, wherein the B cells were avoided to be disturbed in the process of changing the culture medium.

6. Detection by Putting a Cell Culture Dish into a High Content Cell Imager

Figure 5:
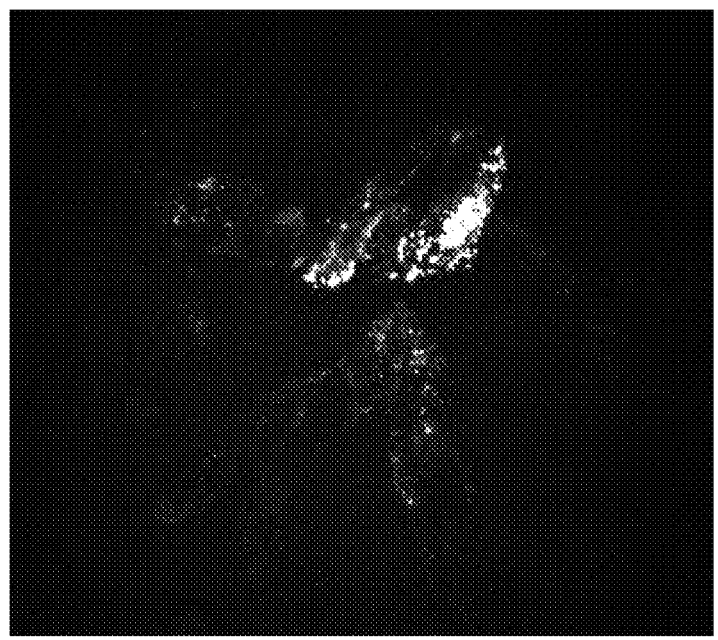
FIG. 5 is a schematic diagram showing that halo is present around B lymphocytes secreting specific anti-PDL1 antibodies.

1) Imaging was performed by using a high content cell imager under a 5-fold microscope, and excitation was conducted with the first exciting light (550 nm-700 nm). The wavelength of the Aleax Flour 647 emitting light was 620 nm-750 nm, from which it can be observed that red halo is present around CHO-K1 cells over-expressing PDL1 around B lymphocytes secreting specific anti-PDL1 antibodies (see FIG. 5). Then, under the 60-fold microscope, the B lymphocytes were photo-activated, the wavelength of the second exciting light (second exciting light) is 365 nm (350 nm-400 nm), and the exposure time is 500 ms (50 ms-5000 ms), which promotes the cells to be photo-activated without light emission.

7. Flow Sorting of Single B Lymphocytes Secreting Specific Antibodies

1) The cells in step 6 were digested into a single-cell suspension, the suspension was sorted by flow cytometry, excited by 500 nm-600 nm exciting light (the maximum exciting wavelength was 572 nm) to obtain the emitting light in an interval of 550 nm-650 nm. (after step 6, the target B cells with halo (secreting target antibodies) were photo-converted to emit red emitting light with a wavelength of 580 nm, B lymphocytes (cannot secrete the target antibody) that were not photo-converted in step 6 do not have fluorescent light), and the photo-converted B lymphocytes (that is, B lymphocytes secreting anti-PDL1 antibody) were sorted to a PCR tube containing cell lysate.

Example 2

This example takes the B lymphocytes secreting the anti-PDL1 antibody screened in example 1 as an example to explain the method for screening the anti-PDL1 antibody. The method includes:

1. Reverse Transcription of a First Strand of cDNA and Amplification of Full-Length cDNA by 5'RACE.
1) Synthesis of first-strand cDNA (SMARTer® RACE 5'/3'Kit, Takara, cat; 634858)
A: Preparation of Reaction System
Mixed Reaction System 1

| Component | Volume |
| --- | --- |
| 5x first chain buffer | 4 µl |
| DTT | 0.5 µl |
| Mixed nucleotide | 1 µl |
| Total | 5.5 µl |

The mixed reaction system 1 was gently mixed with a pipette, and then transiently centrifuged and placed at room temperature.
Mixed Reaction System 2:

| Component | Volume |
| --- | --- |
| RNA | 6 µl |
| mRNA5' cap primer | 1 µl |
| Deionized water | 4 µl |
| Total | 11 µl |

MRNA5' cap primer: AGCAGTGGTATCAACGCAGAGTACrGrGG (as shown in SEQ ID NO: 1).
The mixed reaction system 2 was gently mixed with a pipette, and then transiently centrifuged.
The mixed reaction system 2 was reacted under the following conditions:

| Temperature | Time |
| --- | --- |
| 72° C. | 3 min |
| 42° C. | 2 min |
| Centrifuge at 14000 g | 10 s |

B: Preparation of Reaction System:
Mixed Reaction System 3:

| Component | Volume |
| --- | --- |
| Mixed reaction system 1 | 5.5 µl |
| RNA enzyme inhibitor | 0.5 µl |
| SMARTScribe reverse transcriptase | 2 µl |
| Total | 8 µl |

The mixed reaction system 3 was gently mixed with a pipette, and then transiently centrifuged.
C: Synthesis of First Strand cDNA
Mixed Reaction System 4:

| Component | Volume |
| --- | --- |
| Mixed reaction system 2 | 11 µl |
| Mixed reaction system 3 | 8 µl |
| Oligothymine primer | 1 µl |
| Total | 20 µl |

Oligothymine Primer: AGCAGTGGTATCAACGCAGAGTACTTTTTTTTTT-TTTTTTTTTTTTTTTTTTTTTVN (as shown in SEQ ID NO: 2).
The mixed reaction system 4 was gently mixed with a pipette, and then transiently centrifuged.
Reaction Conditions:

| Temperature | Time |
| --- | --- |
| 42° C. | 90 min |
| 70° C. | 10 min |

D: Amplification of Full-Length cDNA
Mixed Reaction System 5

| Component | Volume |
| --- | --- |
| Deionized water | 15.5 µl |
| 2x SeqAmp buffer | 25 µl |
| SeqAmp DNA polyase | 1 µl |
| Total | 41.5 µl |

The mixed reaction system was gently mixed with a pipette, and then transiently centrifuged.
Mixed Reaction System 6

| Component | Volume |
| --- | --- |
| Mixed reaction system4 | 2.5 µl |
| ISPCR primer | 5 µl |
| Oligothymine primer | 1 µl |
| Mixed reaction system5 | 41.5 µl |
| Total | 50 µl |

Oligothymine Primer: AGCAGTGGTATCAACGCAGAGTACTTTTTTTTT-TTTTTTTTTTTTTTTTTT TTTVN (as shown in SEQ ID NO: 3)
ISPCR primer: AAGCAGTGGTATCAACGCAGAGT (as shown in SEQ ID NO: 4)
PCR Conditions:

| Temperature | Time | Number of cycles |
| --- | --- | --- |
| 94° C. | 30 s | 25x |
| 68° C. | 30 s | |
| 72° C. | 6 min | |

2. The Sequence of the Heavy Chain Variable Region and the Sequence of the Light Chain Variable Region of the Antibody were Obtained by PCR.
Preparation of PCR Reaction System

| Component | System (50 µl) |
| --- | --- |
| 5x Q5 reaction buffer | 10 µl |
| 10 nM mixed nucleotide | 1 µl |
| Forward primer (10 µM) | 1.5 µl (final concentration 0.3 µM) |
| Reward primer (10 µM) | 1 µl (final concentration 0.2 µM) |
| Amplified full-length cDNA | 5 µl |
| GC enhancer | 10 µl |

| Component | System (50 μl) |
|---|---|
| Q5 hot-starting high-fidelity DNA polyase | 0.5 μl |
| dH₂O | 21 μl |

PCR Conditions:

| | | |
|---|---|---|
| 98° C. (pre-denature) | 30 s | 1× |
| 98° C. (denature) | 10 s | 35× |
| 57° C. (anneal) | 30 s | |
| 72° C. (extend) | 30 s | |
| 72° C. (final extend) | 2 min | 1× |
| 4° C. (maintain) | ∞ | |

The forward primer of the heavy chain variable region of the antibody was FVH_Mix (nine 10 μM primers FVH_I-IX were mixed in equal volumes).

The reverse primer of the heavy chain variable region of the heavy chain was RVH_Mix (four 10 μM primers RVH of M_I to IV were mixed in equal volumes). The forward and reverse primers of the heavy chain variable region of the antibody are seen in the following table.

FVH_I
GGCGAGAACTTaTATTTCCAGGGAGAWGTGCAGCTGGTGGAGTC (as shown in SEQ ID NO: 5)

FVH_II
GGCGAGAACTTaTATTTCCAGGGACAGGTGCAGCTGAAGSAGTC (as shown in SEQ ID NO: 6)

FVH_III
GGCGAGAACTTaTATTTCCAGGGAGARGTGAAGCTGGTGGARTC (as shown in SEQ ID NO: 7)

FVH_IV
GGCGAGAACTTaTATTTCCAGGGACAGGTCCAACTGCAGCAGCC (as shown in SEQ ID NO: 8)

FVH_V
GGCGAGAACTTaTATTTCCAGGGASAGGTYCAGCTGCARCAGTC (as shown in SEQ ID NO: 9)

FVH_VI
GGCGAGAACTTaTATTTCCAGGGACAAGTGCAGATGAAGGAGTC (as shown in SEQ ID NO: 10)

FVH_VII
GGCGAGAACTTaTATTTCCAGGGACAGATCCAGTTGGYGCAGTC (as shown in SEQ ID NO: 11)

FVH_VIII
GGCGAGAACTTaTATTTCCAGGGACAGGTCCAACTCCAGCAGCC (as shown in SEQ ID NO: 12)

FVH_IX
GGCGAGAACTTaTATTTCCAGGGACAGGTGCAACTGAAGCAGTC (as shown in SEQ ID NO: 13)

RVH_I
AGGAGGTGTGGTTTTGGCGCTCGAGACGGTGACCGT (as shown in

SEQ ID NO: 14)

RVH_II
AGGAGGTGTGGTTTTGGCGCTCGAGACTGTGAGAGT (as shown in

SEQ ID NO: 15)

RVH_III
AGGAGGTGTGGTTTTGGCGCTCGAGACAGTGACCAG (as shown in

SEQ ID NO: 16)

RVH_IV
AGGAGGTGTGGTTTTGGCGCTCGAGACGGTGACTGA (as shown in

SEQ ID NO: 17)

The forward primer of the light chain variable region of the antibody was FVK_Mix (nine 10 μM primers FVKFK_I-IX were mixed in equal volumes).

The reverse primer of the light chain variable region of the antibody was RVK_Mix (three 10 μM primers RVK of M_I-III were mixed in equal volumes).

The forward and reverse primers of the light chain variable region of the antibody are seen in the following table.

FVK_I
GGCGAGAACTTaTATTTCCAGGGAGAAAWTGTGCTCACCCAGTC (as shown in SEQ ID NO: 18)

FVK_II
GGCGAGAACTTaTATTTCCAGGGACAAATTGTTCTCACCCAGTC (as shown in SEQ ID NO: 19)

FVK_III
GGCGAGAACTTaTATTTCCAGGGARACATTGTGCTGACCCAATC (as shown in SEQ ID NO: 20)

FVK_IV
GGCGAGAACTTaTATTTCCAGGGAGAAACAACTGTGACCCAGTC (as shown in SEQ ID NO: 21)

FVK_V
GGCGAGAACTTaTATTTCCAGGGAGATATTGTGATGACSCAGGC (as shown in SEQ ID NO: 22)

FVK_VI
GGCGAGAACTTaTATTTCCAGGGARRTRTTGTGATGACCCARAC (as shown in SEQ ID NO: 23)

FVK_VII
GGCGAGAACTTaTATTTCCAGGGAGATATCCAGATGACACAGAC (as shown in SEQ ID NO: 24)

FVK_VIII
GGCGAGAACTTaTATTTCCAGGGAGACATTGTGATGACMCAGTC (as shown in SEQ ID NO: 25)

FVK_IX
GGCGAGAACTTaTATTTCCAGGGAGACATCCAGATGACHCAGTC (as shown in SEQ ID NO: 26)

RVK_I
AGGAGCGGCGTCAGCTCTTTTCAGCTCCAGCTTGGTCCC (as shown in SEQ ID NO: 27)

RVK_II
AGGAGCGGCGTCAGCTCTTTTTATTTCCAGTCTGGTCCC (as shown in SEQ ID NO: 28)

RVK_III

AGGAGCGGCGTCAGCTCTTTTKATTTCCARCTTKGTSCC (as shown in SEQ ID NO: 29)

The PCR experiment results are as shown in FIG. 1.

3. The Light and Heavy Chain Variable Regions of the Antibody were Reconstituted to Form a Complete Full-Length Antibody Sequence by Overlap PCR, and In-Vitro Cell-Free Expression was Conducted.

1) The template fragments (5' UTR, IgG1Fc-3' UTR, and IgKc-3' UTR) used for overlap PCR were obtained by PCR.

PCR amplification of 5' UTR fragment system is as follows:

|  | System (50 μl) |
| --- | --- |
| 5× Q5 reaction buffer | 10 μl |
| 10 nM mixed nucleotide | 1 μl |
| Pd2p_up-F (20 μM) | 1.25 μl (final concentration 0.5 μM) |
| TEV-R (20 μM) | 1.25 μl (final concentration 0.5 μM) |
| Plasmid PD2P-1.06 | 1 μl |
| GC enhancer | 10 μl |
| Q5 high-fidelity DNA polyase | 0.5 μl |
| Nuclease-free water | 25 μl |

Pd2p_up-F:

ATCGGTGATGTCGGCGATATAG (as shown in SEQ ID NO: 30);

TEV-R:

TCCCTGGAAATATAAGTTCTCGCC (as shown in SEQ ID NO: 31).

PCR Conditions:

| 98° C. (pre-denature) | 30 s | 1× |
| --- | --- | --- |
| 98° C. (denature) | 10 s | 35× |
| 57° C. (anneal) | 30 s |  |
| 72° C. (extend) | 30 s |  |
| 72° C. (final extend) | 2 min | 1× |
| 4° C. (maintain) | ∞ |  |

PCR amplification of IgG1Fc-3' UTR fragment system is as follows:

| Component | System (50 μl) |
| --- | --- |
| 5× Q5 reaction buffer | 10 μl |
| 10 nM mixed nucleotide | 1 μl |
| IgG1Fc_F2 (20 μM) | 1.25 μl (final concentration 0.5 μM) |
| Pd2p-R (20 μM) | 1.25 μl (final concentration 0.5 μM) |
| Plasmid PGM-IgG1Fc-3'UTR | 1 μl |
| GC enhancer | 10 μl |
| Q5 high-fidelity DNA polyase | 0.5 μl |
| Nuclease-free water | 25 μl |

PCR Conditions:

| 98° C. (pre-denature) | 30 s | 1× |
| --- | --- | --- |
| 98° C. (denature) | 10 s | 35× |
| 57° C. (anneal) | 30 s |  |
| 72° C. (extend) | 30 s |  |
| 72° C. (final extend) | 2 min | 1× |
| 4° C. (maintain) | ∞ |  |

IgG1Fc_F2:

GCCAAAACCACACCTCCT (as shown in SEQ ID NO: 32);

Pd2p-r:

AGCAGCCGGATCGTCGAGTTCG (as shown in SEQ ID NO: 33).

PCR amplification of IgKc-3' UTR fragment system is as follows:

| Component | System (50 μl) |
| --- | --- |
| 5× Q5 reaction buffer | 10 μl |
| 10 nM mixed nucleotide | 1 μl |
| IgKc-F2 (20 μM) | 1.25 μl (final concentration 0.5 uM) |
| Pd2p-R (20 μM) | 1.25 μl (final concentration 0.5 uM) |
| Plasmid PGM-IgKc-3'UTR | 1 μl |
| GC enhancer | 10 μl |
| Q5 high-fidelity DNA polyase | 0.5 μl |
| Nuclease-free water | 25 μl |

IgKc-f2:

AGAGCTGACGCCGCTCCT (as shown in SEQ ID NO: 34);

Pd2p-r:

AGCAGCCGGATCGTCGAGTTCG (as shown in SEQ ID NO: 35).

PCR Conditions:

| 98° C. (pre-denature) | 30 s | 1× |
| --- | --- | --- |
| 98° C. (denature) | 10 s | 35× |
| 57° C. (anneal) | 30 s |  |
| 72° C. (extend) | 30 s |  |
| 72° C. (final extend) | 2 min | 1× |
| 4° C. (maintain) | ∞ |  |

Figure 2:
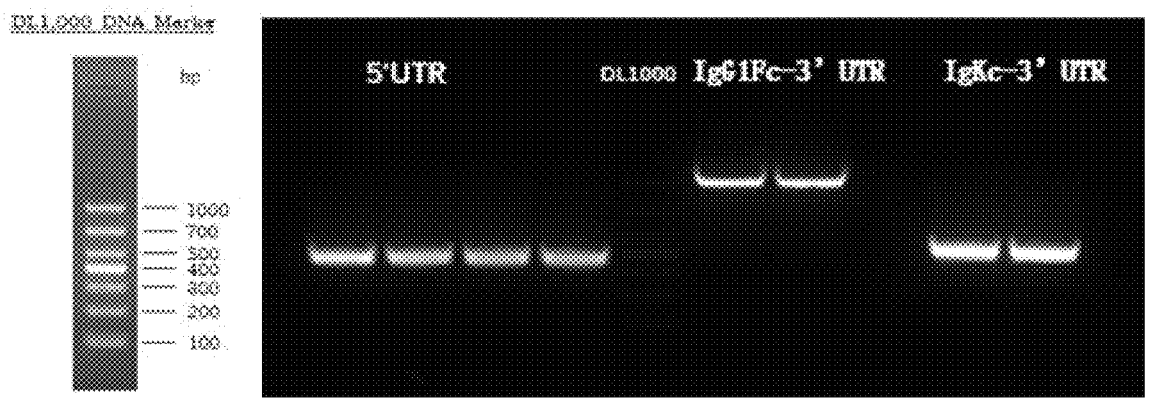
FIG. 2 is a schematic diagram of a 5' untranslated region with a size of about 400 bp, a heavy chain antibody constant region and a 3' untranslated region with a size of about 1200 bp, a light chain antibody constant region and a 3' untranslated region with a size of about 400 bp, which are required for constituting a full-length antibody sequence and obtained by PCR.

The PCR results are as shown in FIG. 2.

2) The variable regions of the light and heavy chains of the antibody were reconstructed into a complete full-length antibody sequence by overlapping PCR

| Component | 50 μl System |
| --- | --- |
| 10× Thermo Pol reaction buffer | 5 μl |
| 10 mM mixed nucleotide | 1 μl |
| pD2P_F (10 μM) | 1.25 μl (0.5 μM) |
| pD2P_R (10 μM) | 1.25 μl (0.5 μM) |
| Template DNA (5' UTR + light/heavy chain variable region + IgG1Fc-3' UTR or IgKc-3' UTR) | 1 μl + 2 μl + 1 μl |

-continued

| Component | 50 μl System |
|---|---|
| Vent DNA polyase | 0.25 μl |
| Nuclease-free water | 37.25 μl | pD2P_F:

ATCGAGATCTCGCGAAATTAATACGA(as shown SEQ ID NO: 36);

pD2P_R:

AGCAGCCGGATCGTCGAGTTCG(as shown SEQ ID NO: 37).

Overlapping PCR Conditions:

| 95° C. (pre-denature) | 30 s | 1x |
|---|---|---|
| 95° C. (denature) | 10 s | 35x |
| 57° C. (anneal) | 30 s | |
| 72° C. (extend) | 30 s | |
| 72° C. (final extend) | 2 min 30 s | 1x |
| 4° C. (maintain) | ∞ | |

Figure 3:
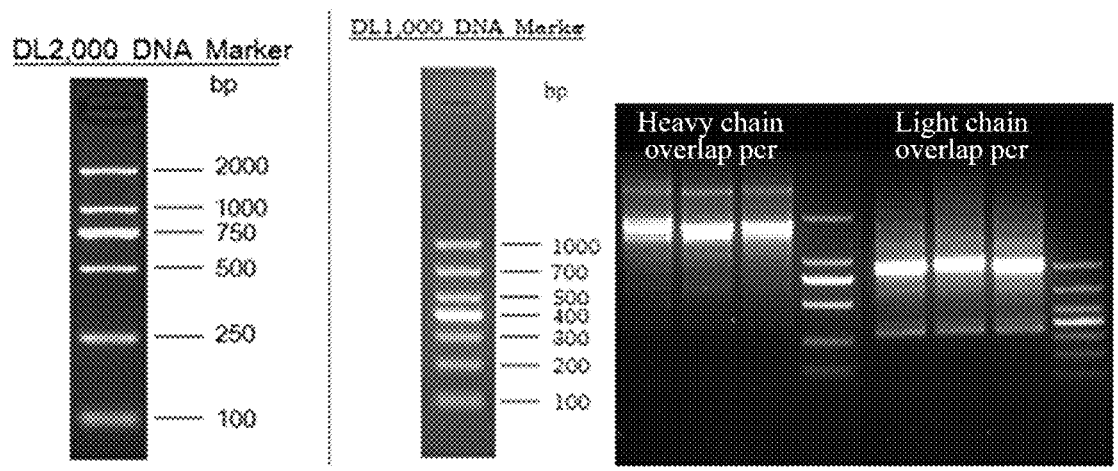
FIG. 3 is a schematic diagram showing that light and heavy chain variable regions of antibody reconstitute a complete full-length antibody sequence by overlap PCR, wherein the full-length antibody sequence has a size of about 1900 bp, and the light chain full-length antibody sequence has a size of about 1000 bp.

The PCR results are as shown in FIG. 3.

3) In-vitro cell-free expression

1 μL of each PCR product of the complete full-length antibody sequences of the light and heavy chains of the antibody obtained by overlap PCR were added into 60 μl of ProteinFactory Rxn (protein factory 1.0) reaction system. After standing for 3-20 hours at 20-30° C., the protein expression can be completed to obtain an anti-PDL1 antibody.

4. Affinity Screening of an Antibody after Obtaining an Expressed Antibody

1) One day in advance, CHO-K1 cells over-expressing PDL1 (10000 cells/well) and CHO-K1 cells over-expressing GFP (2000 cells/well) were taken and mixed in an F-12 culture medium to be inoculated in a 96-well plate with 100 μl/well for culture overnight under the conditions of 37° C. and 5% $CO_2$.

2) The culture medium in the culture plate was aspirated and discarded, and then 40 μl of antibody protein was added in each well to be incubated for 30 min under the conditions of 37° C. and 5% $CO_2$.

3) The protein was aspirated and discarded, and Goal pAb to Ms lgG (Aleax Flour 647, cat: ab150115, abcam) with a working concentration of 0.2 μg/ml and Hoechest 33342 with a working concentration of 0.2 μg/ml were taken and added into the F-12 culture medium (50 μl/well) to be incubated for 30 min under the conditions of 37° C. and 5% $CO_2$.

4) The culture medium was aspirated and discarded, and 50 μl of F-12 culture medium was added.

Figure 4:
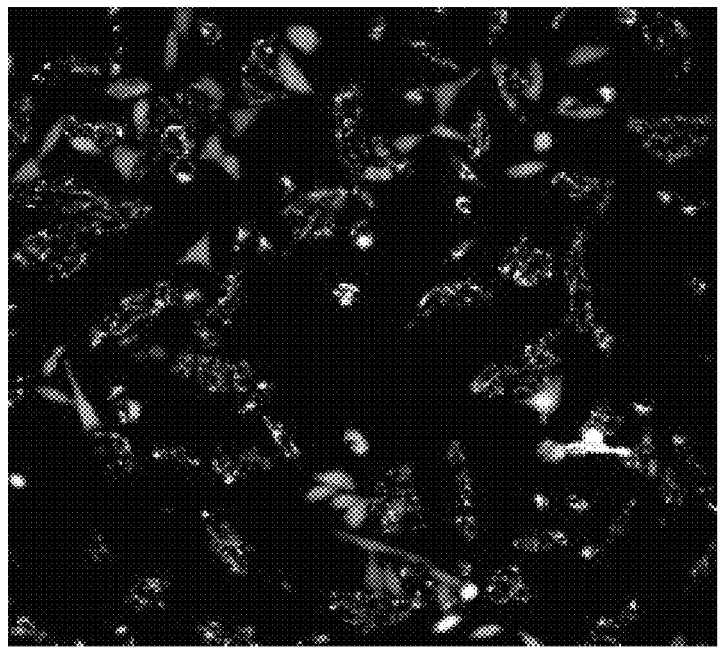
FIG. 4 is a schematic diagram of a labeled antibody labeled by a second fluorescent molecule around a capture antigen by antibody affinity detection using a high content cell imager.

5) High-content shooting was performed and an average fluorescence value (see FIG. 4) was analyzed. The analysis method is as follows:

a) cell nuclei stained with Hoechest 33342 were found by using 350 nm exciting light, and a fluorescence value was adjusted to find total cells.

b) Cells with green fluorescent light were found by using 488 nm exciting light in the cells output in a), and a fluorescence value was adjusted to output CHO-K1-GFP.

c) CHO-K1-GFP in b) was deducted from the total number of cells, and the rest was CHO-K1-PDL1.

d) By using 647 nm exciting light, a red fluorescence value on a cell membrane was detected, and an average red fluorescence value on a CHO-K1-GFP membrane and an average red fluorescence value on a CHO-K1-PDL1 membrane were counted.

e) Affinity screening of antibodies was performed by counting a ratio of the average red fluorescence value on the CHO-K1-PDL1 membrane to the average red fluorescence value on the CHO-K1-GFP membrane. The antibody with a higher ratio was selected, so as to obtain the anti-PDL1 antibody with high affinity.

Example 3

The method for screening B lymphocytes secreting the anti-PDL1 antibody provided in this example is basically the same as that in example 1, except for the step of spreading the transfected B lymphocytes. The operation method in this example is as follows:

1) One day before transfection, a Poly-D-Lysine solution (gibco, REF: A3890401) was diluted to a working concentration of 50 μg/ml using sterile DPBS. In other examples, a semi-solid culture medium or gelatin or the like can also be used in this step.

2) The diluent was added into a six-well plate (this step can increase the adherence of cells), with 2 ml/well.

3) The cells were incubated for 1 hour at room temperature.

4) The diluent was discarded, and the six-well plate was washed three times with sterile water to ensure that the residual Poly-D-Lysine solution diluent was removed.

5) The six-well plate was opened and placed in a biosafety cabinet.

6) After the six-well plate was completely dried, CHO-K1 cells over-expressing PDL1 were spread in the six-well plate.

7) The transfected B lymphocytes were spread into a dish. After culture for 6-48 h, the culture medium was gently aspirated and discarded, and Goat pAb to Ms lgG (Aleax Flour 647, abeam, cat: ab150115) staining solution prepared with a fresh culture medium was added, with a working concentration of 0.2 μg/ml, to avoid disturbing B cells. After incubation for 30 min under the conditions of 37° C. and 5% $CO_2$, the staining solution was gently sucked and discarded, and a fresh culture medium was changed. The process of changing the solution should avoid disturbing B cells.

The other steps are the same as in example 1.

Example 4

The method for screening B lymphocytes secreting the anti-PDL1 antibody provided in this example is basically the same as that in example 1, except that the first fluorescent molecule is PA-GFP protein; in addition, in this example, in the step of high-content cell imaging, the green fluorescent light (the range of the wavelength is 500 nm-600 nm) generated by the candidate cells after being irradiated using intense violet light (350-400 nm) is improved by 100 times; when sorting with flow cytometry, the wavelength range of the exciting light is 450 nm-550 nm (the maximum wavelength of the exciting light is 504 nm), and the wavelength range of the emitting light is 480 nm-600 nm (the maximum wavelength of the emitting light is 517 nm). Photo-activated B lymphocytes secreting the target antibodies and having PA-GFP proteins are labeled and sorted.

Example 5

The method for screening B lymphocytes secreting the anti-PDL1 antibody provided in this example is basically the same as that in example 1. The first fluorescent molecule is Kaede protein; in the step of high-content cell imaging, the candidate cells with green fluorescent light after being irradiated using intense violet light (350-400 nm) to generate green fluorescent light (the range of the wavelength is 500 nm-600 nm) are photo-converted so that the green fluorescent light becomes red fluorescent light (range of the wavelength is 550 nm-650 nm); when sorting with flow cytometry, the wavelength range of the exciting light is 500 nm-600 nm (the maximum wavelength of the exciting light is 572 nm), and the wavelength range of the emitting light is 550 nm-650 nm (the maximum wavelength of the emitting light is 580 nm). Photo-activated B lymphocytes secreting the target antibodies and having Kaede proteins are labeled and sorted.

The above descriptions are only preferred embodiments of the present application, and are not intended to limit the present application. For those skilled in the art, the present application may have various changes and variations. Any modifications, equivalent replacements, improvements and the like made within the spirit and principles of the present application shall be included within the protective scope of the present application.

SEQUENCE LISTING

<110> Suzhou Institute of Nano-Tech and Nano-Bionics (SINANO), Chinese Academy of Sciences
<120> A SCREENING METHOD
<160> 37
<170> patentin version 3.5
<210> 1
<211> 29
<212> DNA
<213> Artificial sequence
<400> 1
agcagtggtatcaacgcagagtacrgrgg 29
<210> 2
<211> 56
<212> DNA
<213> Artificial sequence
<400> 2 agcagtggtatcaacgcagagtactttttttttttttttttttttttttttvn 56
<210> 3
<211> 56
<212> DNA
<213> Artificial sequence
<400> 3
agcagtggtatcaacgcagagtactttttttttttttttttttttttttttvn 56
<210> 4
<211> 23
<212> DNA
<213> Artificial sequence
<400> 4
aagcagtggtatcaacgcagagt
<210> 5
<211> 44
<212> DNA
<213> Artificial sequence
<400> 5
ggcgagaacttatatttccagggagawgtgcagctggtggagtc
<210> 6
<211> 44
<212> DNA
<213> Artificial sequence
<400> 6
ggcgagaacttatatttccagggacaggtgcagctgaagsagtc
<210> 7
<211> 44
<212> DNA
<213> Artificial sequence
<400> 7
ggcgagaacttatatttccagggagargtgaagctggtggartc
<210> 8
<211> 44
<212> DNA
<213> Artificial sequence
<400> 8
ggcgagaacttatatttccagggacaggtccaactgcagcagcc 44
<210> 9
<211> 44
<212> DNA
<213> Artificial sequence
<400> 9
ggcgagaacttatatttccagggasaggtycagctgcarcagtc
<210> 10
<211> 44
<212> DNA
<213> Artificial sequence
<400> 10
ggcgagaacttatatttccagggacaagtgcagatgaaggagtc
<210> 11
<211> 44
<212> DNA
<213> Artificial sequence
<400> 11
ggcgagaacttatatttccagggacagatccagttggygcagtc
<210> 12
<211> 44
<212> DNA
<213> Artificial sequence
<400> 12
ggcgagaacttatatttccagggacaggtccaactccagcagcc
<210> 13
<211> 44
<212> DNA
<213> Artificial sequence
<400> 13
ggcgagaacttatatttccagggacaggtgcaactgaagcagtc
<210> 14
<211> 36
<212> DNA
<213> Artificial sequence
<400> 14
aggaggtgtggttttggcgctcgagacggtgaccgt
<210> 15
<211> 36
<212> DNA
<213> Artificial sequence
<400> 15
aggaggtgtggttttggcgctcgagactgtgagagt
<210> 16
<211> 36
<212> DNA
<213> Artificial sequence
<400> 16
aggaggtgtggttttggcgctcgagacagtgaccag
<210> 17
<211> 36
<212> DNA
<213> Artificial sequence
<400> 17
aggaggtgtggttttggcgctcgagacggtgactga 36

<210> 18
<211> 44
<212> DNA
<213> Artificial sequence
<400> 18
ggcgagaacttatatttccagggagaaawtgtgctcacccagtc 44
<210> 19
<211> 44
<212> DNA
<213> Artificial sequence
<400> 19
ggcgagaacttatatttccagggacaaattgttctcacccagtc 44
<210> 20
<211> 44
<212> DNA
<213> Artificial sequence
<400> 20
ggcgagaacttatatttccagggaracattgtgctgacccaatc 44
<210> 21
<211> 44
<212> DNA
<213> Artificial sequence
<400> 21
ggcgagaacttatatttccagggagaaacaactgtgacccagtc 44
<210> 22
<211> 44
<212> DNA
<213> Artificial sequence
<400> 22
ggcgagaacttatatttccagggagatattgtgatgacscaggc
<210> 23
<211> 44
<212> DNA
<213> Artificial sequence
<400> 23
ggcgagaacttatatttccagggarrtrttgtgatgacccarac
<210> 24
<211> 44
<212> DNA
<213> Artificial sequence
<400> 24
ggcgagaacttatatttccagggagatatccagatgacacagac
<210> 25
<211> 44
<212> DNA
<213> Artificial sequence
<400> 25
ggcgagaacttatatttccagggagacattgtgatgacmcagtc
<210> 26
<211> 44
<212> DNA
<213> Artificial sequence
<400> 26
ggcgagaacttatatttccagggagacatccagatgachcagtc 44
<210> 27
<211> 39
<212> DNA
<213> Artificial sequence
<400> 27
aggagcggcgtcagctcttttcagctccagcttggtccc 39
<210> 28
<211> 39
<212> DNA
<213> Artificial sequence
<400> 28
aggagcggcgtcagctctttttatttccagtctggtccc 39

<210> 29
<211> 39
<212> DNA
<213> Artificial sequence
<400> 29
aggagcggcgtcagctctttkatttccarcttkgtscc 39
<210> 30
<211> 22
<212> DNA
<213> Artificial sequence
<400> 30
atcggtgatgtcggcgatatag 22
<210> 31
<211> 24
<212> DNA
<213> Artificial sequence
<400> 31
tccctggaaatataagttctcgcc
<210> 32
<211> 18
<212> DNA
<213> Artificial sequence
<400> 32
gccaaaaccacacctcct
<210> 33
<211> 22
<212> DNA
<213> Artificial sequence
<400> 33
agcagccggatcgtcgagttcg
<210> 34
<211> 18
<212> DNA
<213> Artificial sequence
<400> 34
agagctgacgccgctcct
<210> 35
<211> 22
<212> DNA
<213> Artificial sequence
<400> 35
agcagccggatcgtcgagttcg
<210> 36
<211> 26
<212> DNA
<213> Artificial sequence
<400> 36
atcgagatctcgcgaaattaatacga
<210> 37
<211> 22
<212> DNA
<213> Artificial sequence
<400> 37
agcagccggatcgtcgagttcg 22

SEQUENCE LISTING

<160> NUMBER OF SEQ ID NOS: 37

<210> SEQ ID NO 1
<211> LENGTH: 29
<212> TYPE: DNA
<213> ORGANISM: Artificial Sequence
<220> FEATURE:
<223> OTHER INFORMATION: The sequence is synthetized.

<400> SEQUENCE: 1
agcagtggta tcaacgcaga gtacrgrgg                                29

<210> SEQ ID NO 2
<211> LENGTH: 56
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (56)..(56)
<223> OTHER INFORMATION: n is a, c, g, or t

<400> SEQUENCE: 2
agcagtggta tcaacgcaga gtactttttt tttttttttt tttttttttt ttttvn     56

<210> SEQ ID NO 3
<211> LENGTH: 56
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (56)..(56)
<223> OTHER INFORMATION: n is a, c, g, or t

<400> SEQUENCE: 3
agcagtggta tcaacgcaga gtactttttt tttttttttt tttttttttt ttttvn     56

<210> SEQ ID NO 4
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 4
aagcagtggt atcaacgcag agt                                      23

<210> SEQ ID NO 5
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 5
ggcgagaact tatatttcca gggagawgtg cagctggtgg agtc               44

<210> SEQ ID NO 6
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 6
ggcgagaact tatatttcca gggacaggtg cagctgaags agtc         44

<210> SEQ ID NO 7
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 7
ggcgagaact tatatttcca gggagargtg aagctggtgg artc         44

<210> SEQ ID NO 8
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 8
ggcgagaact tatatttcca gggacaggtc caactgcagc agcc         44

<210> SEQ ID NO 9
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 9
ggcgagaact tatatttcca gggasaggty cagctgcarc agtc         44

<210> SEQ ID NO 10
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 10
ggcgagaact tatatttcca gggacaagtg cagatgaagg agtc         44

<210> SEQ ID NO 11
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 11
ggcgagaact tatatttcca gggacagatc cagttggygc agtc         44

<210> SEQ ID NO 12
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 12
ggcgagaact tatatttcca gggacaggtc caactccagc agcc         44

<210> SEQ ID NO 13
<211> LENGTH: 44
<212> TYPE: DNA

<213> ORGANISM: Artificial Sequence
<220> FEATURE:
<223> OTHER INFORMATION: The sequence is synthetized.

<400> SEQUENCE: 13
ggcgagaact tatatttcca gggacaggtg caactgaagc agtc        44

<210> SEQ ID NO 14
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 14
aggaggtgtg gttttggcgc tcgagacggt gaccgt        36

<210> SEQ ID NO 15
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 15
aggaggtgtg gttttggcgc tcgagactgt gagagt        36

<210> SEQ ID NO 16
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 16
aggaggtgtg gttttggcgc tcgagacagt gaccag        36

<210> SEQ ID NO 17
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 17
aggaggtgtg gttttggcgc tcgagacggt gactga        36

<210> SEQ ID NO 18
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 18
ggcgagaact tatatttcca gggagaaawt gtgctcaccc agtc        44

<210> SEQ ID NO 19
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 19
ggcgagaact tatatttcca gggacaaatt gttctcaccc agtc        44

<210> SEQ ID NO 20
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 20
ggcgagaact tatatttcca gggaracatt gtgctgaccc aatc        44

<210> SEQ ID NO 21
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 21
ggcgagaact tatatttcca gggagaaaca actgtgaccc agtc        44

<210> SEQ ID NO 22
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 22
ggcgagaact tatatttcca gggagatatt gtgatgacsc aggc        44

<210> SEQ ID NO 23
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 23
ggcgagaact tatatttcca gggarrtrtt gtgatgaccc arac        44

<210> SEQ ID NO 24
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 24
ggcgagaact tatatttcca gggagatatc cagatgacac agac        44

<210> SEQ ID NO 25
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 25
ggcgagaact tatatttcca gggagacatt gtgatgacmc agtc        44

<210> SEQ ID NO 26
<211> LENGTH: 44
<212> TYPE: DNA
<213> ORGANISM: Artificial Sequence
<220> FEATURE:

<223> OTHER INFORMATION: The sequence is synthetized.

<400> SEQUENCE: 26
ggcgagaact tatatttcca gggagacatc cagatgachc agtc         44

<210> SEQ ID NO 27
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 27
aggagcggcg tcagctcttt tcagctccag cttggtccc              39

<210> SEQ ID NO 28
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 28
aggagcggcg tcagctcttt ttatttccag tctggtccc              39

<210> SEQ ID NO 29
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 29
aggagcggcg tcagctcttt tkatttccar cttkgtscc              39

<210> SEQ ID NO 30
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 30
atcggtgatg tcggcgatat ag                                22

<210> SEQ ID NO 31
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 31
tccctggaaa tataagttct cgcc                              24

<210> SEQ ID NO 32
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 32
gccaaaacca cacctcct                                     18

```
<210> SEQ ID NO 33
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 33
agcagccgga tcgtcgagtt cg                                              22

<210> SEQ ID NO 34
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 34
agagctgacg ccgctcct                                                   18

<210> SEQ ID NO 35
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 35
agcagccgga tcgtcgagtt cg                                              22

<210> SEQ ID NO 36
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 36
atcgagatct cgcgaaatta atacga                                          26

<210> SEQ ID NO 37
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 37
agcagccgga tcgtcgagtt cg                                              22
```

What is claimed is:

1. A method for screening cells secreting target antibodies, comprising the following steps:
    step (a): labeling a candidate cell with a first fluorescent molecule;
    step (b): adding the candidate cell labeled with the first fluorescent molecule and a labeled antibody against the target antibodies into a container fixed with a capture antigen to be mixed and incubated to obtain a cellular fluid; wherein the capture antigen is configured to specifically bind to the target antibodies; the labeled antibody is labeled with a second fluorescent molecule;
    the first fluorescent molecule has the following properties:
        a fluorescent light emitted after the first fluorescent molecule is excited by a first exciting light is different from a fluorescent light emitted after the second fluorescent molecule is excited by the first exciting light; the first fluorescent molecule is in a photo-activated state or a photo-converted state, the first fluorescent molecule emits a first fluorescent light after being excited by a third exciting light under the photo-activated state or the photo-converted state; the first fluorescent molecule emits a second fluorescent light after being directly excited by the third exciting light instead of a second exciting light; a wavelength of the first fluorescent light is different from a wavelength of the second fluorescent light, or a wavelength of the first fluorescent light is the same as a wavelength of the second fluorescent light but fluorescence intensities are different; wherein a wavelength of the first exciting light is different from a wavelength of the second exciting light; the wavelength of the second exciting light is different from a wavelength of the third exciting light;

a wavelength of the fluorescent light emitted after the second fluorescent molecule is excited by the first exciting light is different from the wavelength of the second exciting light;

step (c): observing the cellular fluid using a high content cell imager, exciting the second fluorescent molecule by using the first exciting light to emit the fluorescent light and screening the candidate cell surrounded by the fluorescent light, and labeling the candidate cell as a target candidate cell; then irradiating the target candidate cell with the second exciting light so that the first fluorescent molecule labeling the target candidate cell is in the photo-activated state or the photo-converted state;

step (d): sorting the candidate cell in the cellular fluid using a flow cytometry, wherein in a process of sorting, the candidate cell processed in step (c) is irradiated using the third exciting light and the target candidate cell emitting the first fluorescent light is sorted, namely, the cells secreting the target antibodies.

2. The method according to claim 1, wherein the first fluorescent molecule is one selected from the group consisting of a photo-activated fluorescent protein and a photo-converted fluorescent protein.

3. The method according to claim 2, wherein in step (d), when the cellular fluid is used to flow through the flow cytometry for sorting, the second fluorescent molecule is a fluorescent molecule not emitting the fluorescent light under an excitation of the third exciting light, or a fluorescent molecule emitting the fluorescent light under an excitation of the third exciting light having a wavelength different from the wavelength of the first fluorescent light.

4. The method according to claim 3, wherein the photo-activated fluorescent protein is PA-GFP;
a range of the wavelength of the first exciting light is not within a range of 390 nm-415 nm, a range of the wavelength of the second exciting light is 390 nm-450 nm, and a range of the wavelength of the third exciting light is 450 nm-550 nm.

5. The method according to claim 4, wherein the candidate cell in step (a) is selected from the group consisting of B lymphocytes, T cells, NK cells, HEK cells, CHO cells, bacteria, and yeast.

6. The method according to claim 4, wherein in step (a), a method for labeling the candidate cell with the first fluorescent molecule is one selected from the group consisting of the following (I)-(IV):
(I): introducing a nucleotide encoding the first fluorescent molecule into the candidate cell and allowing the nucleotide to express the first fluorescent molecule in the candidate cell;
(II): introducing the first fluorescent molecule into the candidate cell through an electrotransfection;
(III): performing a fusion expression on the first fluorescent molecule and an antibody of a cytomembrane surface specific marker of the candidate cell, so that the first fluorescent molecule is linked to a surface of the candidate cell through a specific binding of the antibody to the cytomembrane surface specific marker; and
(IV): labeling the first fluorescent molecule with a lipid, mixing the first fluorescent molecule labeled with the lipid with the candidate cell so that the first fluorescent molecule is linked to a surface of the candidate cell.

7. The method according to claim 3, wherein the photo-converted fluorescent protein is one selected from the group consisting of PS-CFP2, PS-CFP, mEosFP, tdEosFP, dEosFP, WtEosFP, Kaede, Dendra2, and KikGR.

8. The method according to claim 7, wherein the first fluorescent molecule is a PS-CFP2 protein, a range of the wavelength of the first exciting light is not within a range of 390 nm-450 nm, a range of the wavelength of the second exciting light is 390 nm-415 nm, and a range of the wavelength of the third exciting light is 420 nm-520 nm;
or, the first fluorescent molecule is a Kaede protein, a range of the wavelength of the first exciting light is not within a range of 350 nm-400 nm, a range of the wavelength of the second exciting light is 350 nm-400 nm, and a range of the wavelength of the third exciting light is 500 nm-600 nm;
or, the first fluorescent molecule is a KikGR protein, a range of the wavelength of the first exciting light is not within a range of 390 nm-415 nm, a range of the wavelength of the second exciting light is 390 nm-415 nm, and a range of the wavelength of the third exciting light is 500 nm-600 nm.

9. The method according to claim 8, wherein the candidate cell in step (a) is selected from the group consisting of B lymphocytes, T cells, NK cells, HEK cells, CHO cells, bacteria, and yeast.

10. The method according to claim 8, wherein in step (a), a method for labeling the candidate cell with the first fluorescent molecule is one selected from the group consisting of the following (I)-(IV):
(I): introducing a nucleotide encoding the first fluorescent molecule into the candidate cell and allowing the nucleotide to express the first fluorescent molecule in the candidate cell;
(II): introducing the first fluorescent molecule into the candidate cell through an electrotransfection;
(III): performing a fusion expression on the first fluorescent molecule and an antibody of a cytomembrane surface specific marker of the candidate cell, so that the first fluorescent molecule is linked to a surface of the candidate cell through a specific binding of the antibody to the cytomembrane surface specific marker; and
(IV): labeling the first fluorescent molecule with a lipid, mixing the first fluorescent molecule labeled with the lipid with the candidate cell so that the first fluorescent molecule is linked to a surface of the candidate cell.

11. The method according to claim 7, wherein the candidate cell in step (a) is selected from the group consisting of B lymphocytes, T cells, NK cells, HEK cells, CHO cells, bacteria, and yeast.

12. The method according to claim 7, wherein in step (a), a method for labeling the candidate cell with the first fluorescent molecule is one selected from the group consisting of the following (I)-(IV):
(I): introducing a nucleotide encoding the first fluorescent molecule into the candidate cell and allowing the nucleotide to express the first fluorescent molecule in the candidate cell;
(II): introducing the first fluorescent molecule into the candidate cell through an electrotransfection;
(III): performing a fusion expression on the first fluorescent molecule and an antibody of a cytomembrane surface specific marker of the candidate cell, so that the first fluorescent molecule is linked to a surface of the candidate cell through a specific binding of the antibody to the cytomembrane surface specific marker; and (IV): labeling the first fluorescent molecule with a lipid, mixing the first fluorescent molecule labeled with the lipid with the candidate cell so that the first fluorescent molecule is linked to a surface of the candidate cell.

13. The method according to claim 3, wherein the candidate cell in step (a) is selected from the group consisting of B lymphocytes, T cells, NK cells, HEK cells, CHO cells, bacteria, and yeast.

14. The method according to claim 3, wherein in step (a), a method for labeling the candidate cell with the first fluorescent molecule is one selected from the group consisting of the following (I)-(IV):
- (I): introducing a nucleotide encoding the first fluorescent molecule into the candidate cell and allowing the nucleotide to express the first fluorescent molecule in the candidate cell;
- (II): introducing the first fluorescent molecule into the candidate cell through an electrotransfection;
- (III): performing a fusion expression on the first fluorescent molecule and an antibody of a cytomembrane surface specific marker of the candidate cell, so that the first fluorescent molecule is linked to a surface of the candidate cell through a specific binding of the antibody to the cytomembrane surface specific marker; and
- (IV): labeling the first fluorescent molecule with a lipid, mixing the first fluorescent molecule labeled with the lipid with the candidate cell so that the first fluorescent molecule is linked to a surface of the candidate cell.

15. The method according to claim 2, wherein in step (a), a method for labeling the candidate cell with the first fluorescent molecule is one selected from the group consisting of the following (I)-(V):
- (I): introducing a nucleotide encoding the first fluorescent molecule into the candidate cell and allowing the nucleotide to express the first fluorescent molecule in the candidate cell;
- (II): introducing the first fluorescent molecule into the candidate cell through an electrotransfection;
- (III): performing a fusion expression on the first fluorescent molecule and an antibody of a cytomembrane surface specific marker of the candidate cell, so that the first fluorescent molecule is linked to a surface of the candidate cell through a specific binding of the antibody to the cytomembrane surface specific marker; and
- (IV): labeling the first fluorescent molecule with a lipid, mixing the first fluorescent molecule labeled with the lipid with the candidate cell so that the first fluorescent molecule is linked to a surface of the candidate cell.

16. The method according to claim 15, wherein the lipid is selected from DSPE-NHS, DSPE-PEG2000-NHS, DSPE-PEG3400-NHS, oleyl-PEG2000-NHS, oleyl-PEG4000-NHS, and DOPE-PEG2000-NHS.

17. The method according to claim 2, wherein the candidate cell in step (a) is selected from the group consisting of B lymphocytes, T cells, NK cells, HEK cells, CHO cells, bacteria, and yeast.

18. The method according to claim 1, wherein the candidate cell in step (a) is selected from the group consisting of B lymphocytes, T cells, NK cells, HEK cells, CHO cells, bacteria, and yeast.

19. A method for screening target antibodies, comprising the following steps:
- obtaining the cells secreting the target antibodies using the method according to claim 1; and
- acquiring a nucleotide sequence encoding the target antibodies from the cells secreting the target antibodies.

20. The method according to claim 19, wherein the first fluorescent molecule is one selected from the group consisting of a photo-activated fluorescent protein and a photo-converted fluorescent protein.

* * * * *